United States Patent [19]

Kato et al.

[11] Patent Number: 4,744,648
[45] Date of Patent: May 17, 1988

[54] EYE REFRACTIVE POWER MEASURING APPARATUS

[75] Inventors: Yasuo Kato; Yasufumi Fukuma; Kiwami Horiguchi; Kiichi Kamiyama, all of Tokyo, Japan

[73] Assignee: Tokyo Kogaku Kikai Kabushiki Kaisha, Itabashi, Japan

[21] Appl. No.: 866,247

[22] Filed: May 23, 1986

[30] Foreign Application Priority Data

May 24, 1985 [JP] Japan ............... 60-111538

[51] Int. Cl.$^4$ ............................................. A61B 3/10
[52] U.S. Cl. ............................. 351/211; 351/208; 351/210
[58] Field of Search ............... 351/211, 208, 214, 221, 351/210

[56] References Cited

U.S. PATENT DOCUMENTS

| | | | |
|---|---|---|---|
| 4,196,979 | 4/1980 | Kohayakawa | 351/211 |
| 4,408,847 | 10/1983 | Wada | 351/211 |
| 4,432,617 | 2/1984 | Itoh | 351/211 |

Primary Examiner—Rodney B. Bovernick
Assistant Examiner—Jay P. Ryan
Attorney, Agent, or Firm—Finnegan, Henderson, Farabow, Garrett & Dunner

[57] ABSTRACT

An improved eye refractive power measuring apparatus is disclosed. The apparatus includes a measurement system for projecting a measurement target image to the retina of an eye to be tested and measuring the refractivity of the eye to be tested by detecting the focussing state of the measuring target image. In addition, it has an eye position detection system for detecting a shifted amount from a proper position of the eye to be tested and an arrangement for correcting a measurement result of the eye refractivity based on such detected result.

4 Claims, 10 Drawing Sheets

EYE REFRACTIVE POWER MEASURING APPARATUS

BACKGROUND OF THE INVENTION

This invention relates to an eye refractive power measuring apparatus for detecting refractivity of an eye to be tested by projecting a measurement target image to the retina thereof and detecting a focussing state of the measurement target image.

In a conventional eye refractive power measuring apparatus, it has been heretofore required to properly set the measurement optical axis of a measuring optical system with respect to the eye to be tested, to reduce errors in the measurement result. In order to avoid the occurrence of such errors and improve measurement accuracy, an arrangement has been made such that an alignment of the measurement optical system with respect to the eye to be tested is effected before the eye to be tested is measured, by projecting a measurement flux of rays toward the eye to be tested from the measurement optical system.

Figure 1:
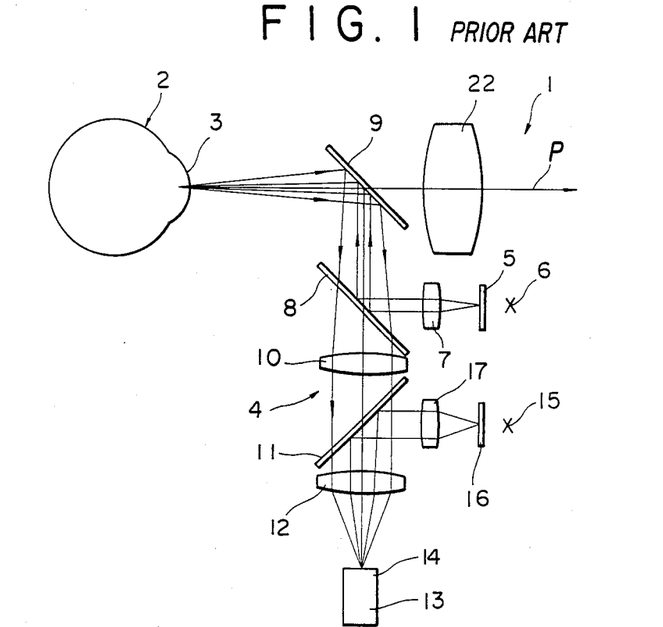
FIG. 1 is a schematic illustration of an optical system for explaining alignment verification of a conventional eye refractive power measuring apparatus.
Figure 2:
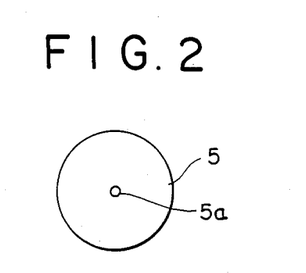
FIG. 2 is a plan view of an alignment target plate shown in FIG. 1.
Figure 3:
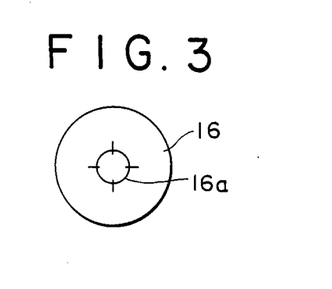
FIG. 3 is a plan view of a reference pattern shown in FIG. 1.
Figure 4:
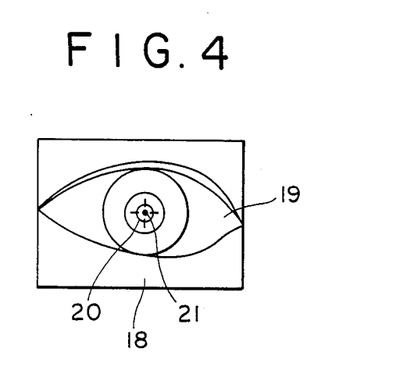
FIG. 4 is an illustration showing the target of the system of FIG. 1 displayed on a television monitor.

For example, as shown in FIG. 1, in the conventional apparatus, there is provided an alignment target projection system 4 for projecting an alignment target flux of rays toward a cornea 3 of the eye 2 to be tested. The alignment system 4 is separate from a measurement optical system 1. An alignment target plate 5 (see FIG. 2) is illuminated by an illumination light source 6, the light transmitted through a circular pin hole 5a of the alignment target plate 5 is converted into a parallel pencil of rays and guided to the eye 2 to be tested as an alignment target flux of rays through half mirrors 8 and 9 to form a virtual image on the cornea 3. Reflection rays forming the virtual image on the cornea 3 are guided to an imaging lens 12 through the half mirrors 8 and 9, a relay lens 10, and a half mirror 11. An alignment target image is imaged on a photosensitive surface 14 of a photosensitive element 13 by the imaging lens 12 together with an anterior portion image, of the eye. A reference pattern (see FIG. 3) is illuminated by an illumination light source 15 with the light transmitted through a circular cross pattern 16a thereof being converted into parallel pencils of rays by a projection lens 17, and guided to the imaging lens 12 as a reference pattern flux of rays through the half mirror 11 and imaged on the photosensitive surface 14 of the photosensitive element 13 as a reference pattern image by the imaging lens 12. The anterior portion image, the alignment target image and the reference pattern image are converted into an electrical signal by the photosensitive element 13. The anterior portion image 19, the reference pattern image 20 and the alignment target image 21 are displayed on a display surface 18 of a television monitor as shown in FIG. 4. Positional alignment of a measurement optical axis of the measurement optical system within a plane intersecting the measurement optical axis at right angles is then verified by confirming the image displayed on the screen. At the same time, a distance in the optical axis direction or working distance of the measurement optical axis with respect to the eye 2 to be tested is adjusted based on the sharpness of the alignment target image 21. In FIG. 1, reference numeral 22 denotes an objective lens of the measurement optical system 1.

However, the above-mentioned conventional apparatus has presented crucial disadvantages or drawbacks in that a judgement of whether the measurement optical system is properly set with respect to the eye to be tested is not easy. Moreover, adjustment of the working distance in the optical axis direction is troublesome, since the adjustment of the measurement optical axis direction distance of the measurement optical system is effected by judging whether the target image is sharply formed, i.e., whether it is in focus. Although there is proposed another apparatus, in which a pair of target images are visually confirmed in the separated state when the measurement optical system is not properly set with respect to the eye to be tested, and the images are visually confirmed in an overlapping state when the system is properly set, such as system has the shortcomings that it is difficult to judge the separating amount of the pair of target images in the vicinity of the optical axis direction distance when the measurement optical system is properly set with respect to the eye to be tested (the term "vicinity" refers to a small difference between the optical axis direction distance when the measurement optical system is properly set with respect to the eye to be tested and that when the system is improperly set). At any rate, it is a difficult job to adjust the working distance by properly setting the measurement optical system with respect to the eye to be tested, and none of the conventional apparatuses are capable of performing the measurement of refractivity of an eye to be tested both promptly and accurately.

SUMMARY OF THE INVENTION

The present invention is accomplished in order to remove the above-mentioned disadvantages of the conventional apparatuses by providing an improved and novel eye refractive power measuring apparatus, wherein even if an optical axis direction distance of a measurement optical system is not properly set with respect to an eye to be tested, there can be prevented an occurrence of measurement errors caused by improper setting of the measurement optical system with respect to the eye to be tested in, thereby enabling a speedy and accurate measurement.

The present invention is accomplished in view of the fact that there exists a correlation between a shifted amount from an optical axis direction distance when a measurement optical system is properly set with respect to an eye to be tested (i.e., the difference between the optical axis direction distance when the measurement optical system is properly set with respect to the eye to be tested and that when the system is improperly set) and measurement errors of refractivity. The present invention includes an eye refractive power measuring apparatus including a measurement system for projecting a measurement target image to the retina of an eye to be tested and measuring the refractivity of the eye to be tested by detecting the focussing state of the measurement target image. The improvement comprising an eye position detection system for detecting a shifted amount from a proper position of the eye to be tested in the axial direction of the measurement system, and correction means for correcting a measurement result of the refractivity based on such detected shifted amount.

According to the eye refractive power measuring apparatus of the present invention, adjustment of the optical axis direction distance of the measurement optical system with respect to the eye to be tested is effected within a range in which a large displacement is not taken from the optical axis direction distance when the measurement optical system is properly set with respect to the eye to be tested. The adjustment is made before measurement of the eye to be tested is effected by projecting a measurment flux of rays toward the eye to be tested by the measurement optical system. If any shift occurs at this time, the shifted amount is measured by the eye position detection system and based on such obtained detection result of the shifted amount, the measurement result of refractivity of the eye to be tested is corrected.

The above and other objects, features and advantages of the present invention will become more apparent to those skilled in the art from the following detailed description of the preferred embodiment of the present invention, when taken in conjunction with the accompanying drawings, wherein:

DETAILED DESCRIPTION OF THE EMBODIMENT

One preferred embodiment of the present invention will be described hereunder with reference to the accompanying drawings.

Figure 5:
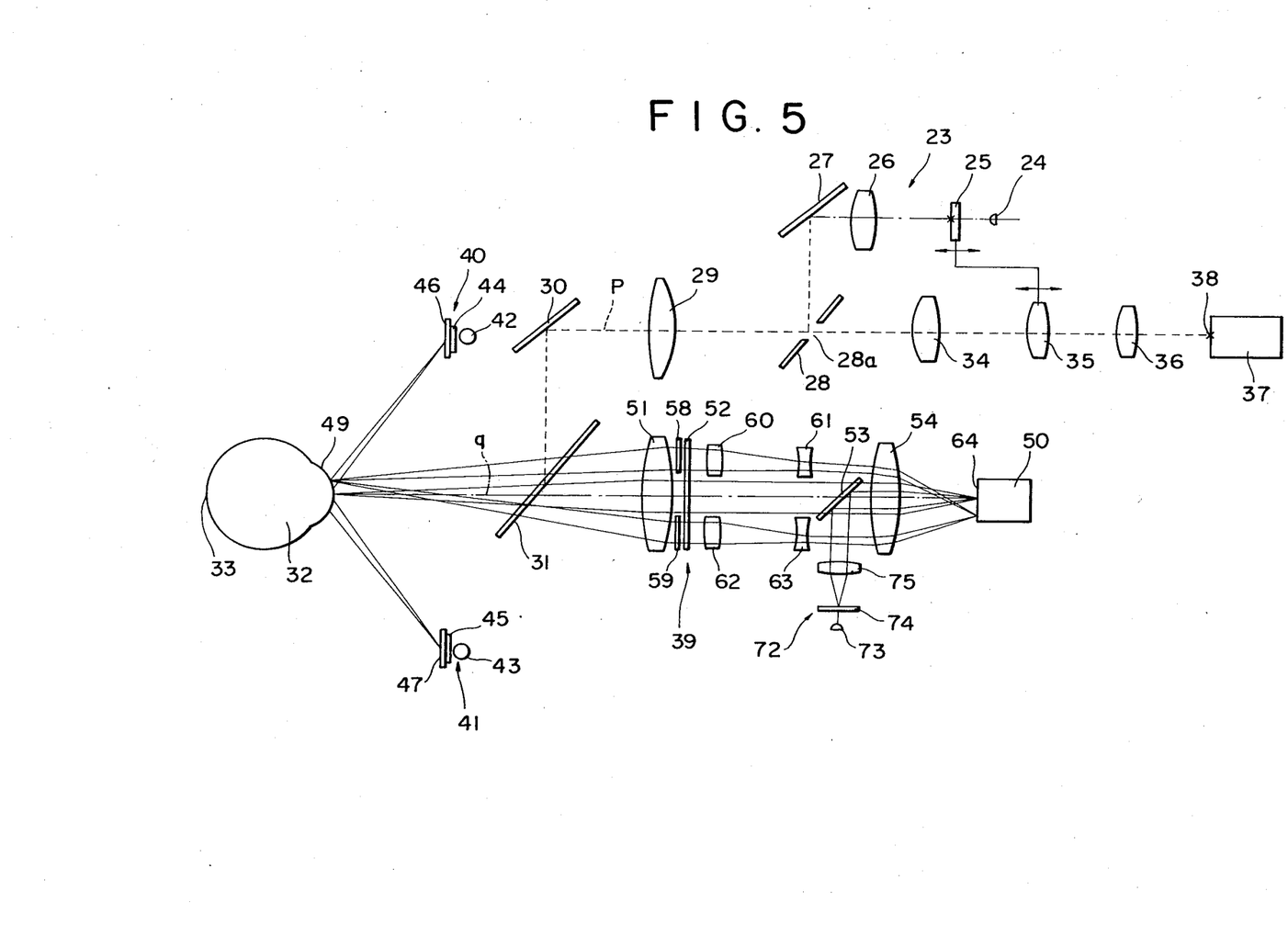
FIG. 5 is a schematic illustration of an optical system showing the construction of an important portion of an eye refractive power measuring apparatus according to one embodiment of the present invention.
Figure 6:
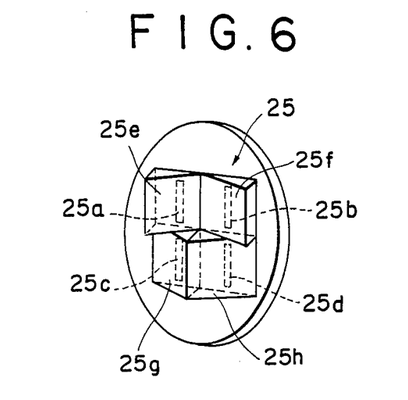
FIG. 6 is an enlarged illustration of a measurement target plate shown in FIG. 5.

FIG. 5 illustrates one preferred embodiment of an eye refractive power measuring apparatus according to the present invention. For the purpose of convenience, an automatic refractometer functioning as the eye refractive power measuring apparatus will be described here. In FIG. 5, reference numeral 23 generally denotes a measurement optical system, in which a flux of rays from a measurement target plate 25 illuminated by an illumination light source 24 is projected toward an eye 32 to be tested through a relay lens 26, a reflection mirror 27, a perforated mirror 28, an objective lens 29, a reflection mirror 30 and a half mirror 31 to form a measurement target image on its retina 33. In this embodiment, the target plate 25, as shown in its enlarged form in FIG. 6, is formed with slits 25a-25d. These slits 25a-25d are attached with four deflection prisms 25e-25h. The arrangement being such that when the target plate 25 is moved along the optical axis and the measurement target image is focussed on the retina 33, the distances between a pair of upper and lower slit images of a measurement target image on the retina 33 become equal.

The flux of rays from the measurement target image on the retina 33 passes through a half mirror 31, a reflection mirror 30, an objective lens 29, and a perforated portion 28a of the perforated mirror 28 and is caused to form a measurement target image on a photosensitive surface 38 of a photosensitive element 37 by relay lenses 34, 35 and an imaging lens 36. The relay lens 35 is reciprocally movable in the optical axis direction integrally with the measurement target plate 25. The measurement target plate 25 and the photosensitive surface 38 are held in optically conjugate relation.

Due to the foregoing construction, the measurement target plate 25 and the relay lens 35 are integrally moved to a position where the distances between the pair of upper and lower slit images of the measurement target image formed on the photosensitive surface 38 become equal. The upper and lower slit images are monitored in accordance with an electrical signal of a photosensitive element 37 as will be described later. The images become equal at a position where the measurement target image is caused to be focussed on the retina 33. The and the refractivity of the eye 32 to be tested is measured according to the amount the target plate 25 and relay lens 35 are moved.

Next, an eye position detection optical system 39 will be described. This eye position detection optical system 39 has such a function as to form a positioning target image to be used for positioning the measurement optical axis p of the measurement optical system 23, and the target image to be used for adjusting the optical axis direction distance of the measurement optical system 23 with respect to the eye 32, on an image pick-up apparatus. A pair of target image projection means 40 and 41 are disposed at symmetical positions in front of the eye 32 to be tested with a detection optical axis q of the eye position detection optical system 39 interposed therebetween.

Figure 7:
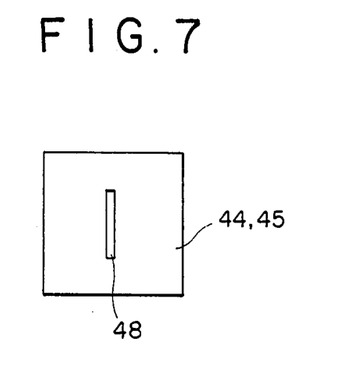
FIG. 7 is a plan view of the target plate shown in FIG. 5.
Figure 8:
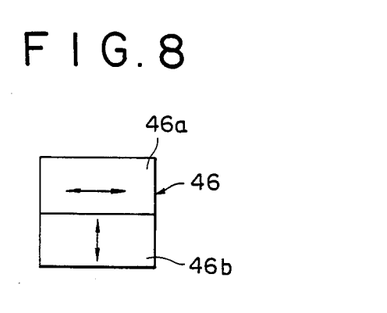
FIGS. 8 and 9 are plan views of a polarization plate shown in FIG. 5.
Figure 9:
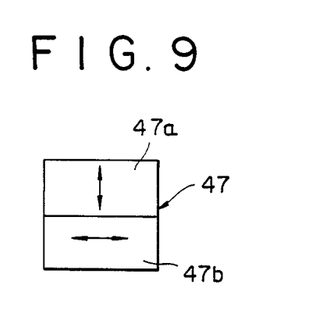

These target image projection means 40 and 41 have such a function as to project a flux of target rays, for effecting an adjustment of the optical axis direction distance of the measurement optical system 23 with respect to the eye 32, to the right side and the left side portions of the eye 32 with the pupil placed therebetween. The target image projection means 40 and 41 respectively comprise illumination light sources 42, 43, target plates 44, 45, and polarization plates 46, 47. The target plates 44 and 45 are each formed with a vertically elongated slit 48 as shown in FIG. 7. The polarization plates 46 and 47 respectively comprise dividing polarization plates 46a, 46b, 47a and 47b, in which the polarization axes intersect at right angles with respect to each other as shown in FIGS. 8 and 9. The illumination light passes through the elongated slit 48 and becomes a flux of target rays. The flux of target rays is projected to a corneal surface 49 of the eye 32 to form a rectangle-shaped target virtual image corresponding to the slit 48 thereon.

In this embodiment, the upper half portion of the rectangle-shaped target virtual image formed by the target image projection means 41 is formed of only light having a horizontal direction polarization ingredient, while the lower half portion thereof is formed of only light having a vertical direction polarization ingredient. The upper half portion of the rectangle-shaped target virtual image formed by the target image projection means 42 is formed of only light having the vertical direction ingredient, while the lower half portion thereof is formed of only light having the horizontal direction ingredient.

Figure 10:
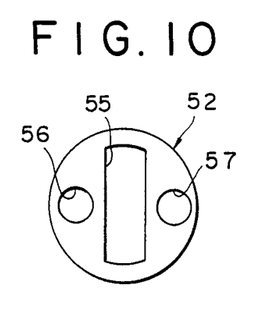
FIG. 10 is a plan view of a diaphragm plate shown in FIG. 5.
Figure 11:
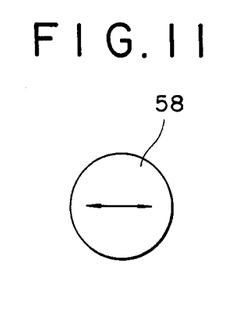
FIGS. 11 and 12 are plan views of an analyzer shown in FIG. 5.
Figure 12:
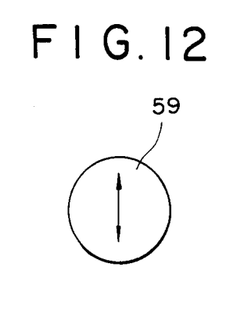

A photosensitive element 50 is disposed on the detection optical axis q of the eye position detection optical system 39. Between the half mirror 31 and the photosensitive element 50, an objective lens 51, a diaphragm plate 52, a half mirror 53 and an imaging lens 54 are disposed. With reference to FIG. 10, the diaphragm plate 52 includes a vertically elongated through hole 55 at its central portion and small circular holes 56, 57 each at the both sides thereof. This diaphragm plate 52 has such a function as to divide the detection optical path of the target virtual image into two optical paths and is provided with analyzers 58, 59 facing to the small circular holes 56, 57, respectively. The analyzer 58 permits only the light having the horizontal direction polarization ingredient to transmit as shown in FIG. 11, while the other analyzer 59 permits only the light having the vertical direction polarization ingredient to transmit as shown in FIG. 12. In the mid-way of the optical path through analyzer 58, a convex lens 60 and a concave lens 61 are disposed between the diaphragm plate 52 and the imaging lens 54. On the other hand, in the mid-way of the optical path through analyzer 59, a convex lens 62 and a concave lens 63 are disposed between the diaphragm plate 52 and the imaging lens 54. These convex lenses 60, 62, and concave lenses 61, 63 respectively are arranged in symmetrical positions with the detection optical axis q disposed therebetween, thereby forming a Galileo variable power system. This Galileo variable power system has such a function as to enlarge the target image and form it on the photosensitive surface 64 of the photosensitive element 50.

The anterior portion of the eye 32 to be tested is illuminated by illumination light. Reflection light reflected by the anterior portion is converted into a parallel pencil of rays by the objective lens 51 and guided the imaging lens 54 passing through the through hole 55 of the diaphragm 52. As a result, an image of the anterior portion is formed on the photosensitive surface 64 of the photosensitive element 50 together with the target image. Both the anterior portion image and the target image formed on the photosensitive surface 64 of the photosensitive element 50 are displayed on the screen of a television monitor as will be described later.

Figure 13:
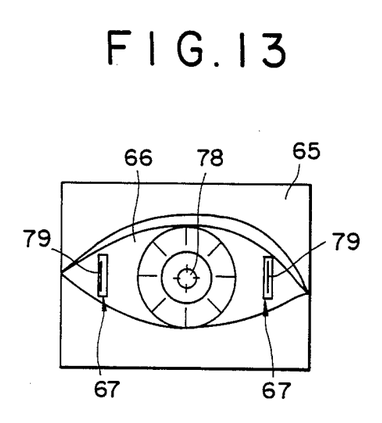
FIGS. 13 through 15 are illustrations of a display board of a television monitor on which an anterior portion image, and other images are displayed utilizing an eye position detecting optical system according to the present invention.
Figure 14:
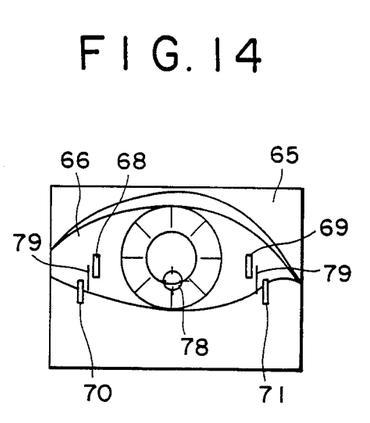
Figure 15:
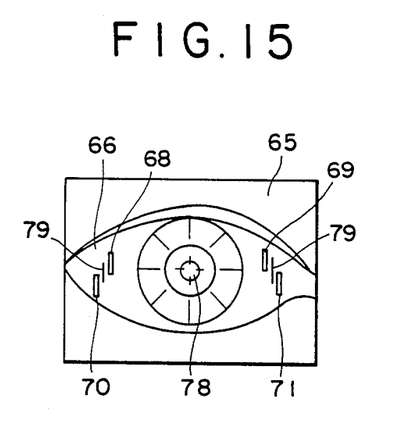

FIGS. 13 through 15 illustrate the anterior portion image and the target image displayed on the screen 65 of the television monitor. Although the photosensitive element 37 on which the measurement target image is projected and the photosensitive element 50 on which both the anterior portion image and the target image are projected are separately provided in this embodiment, one photosensitive element may be used for double purposes by guiding both the images to the one photosensitive element using a half mirror for instance. In FIGS. 13 through 15, 66 denotes an anterior portion image and 67 denotes target images. The target images respectively comprise upper target images 68, 69 and lower target images 70, 71. As shown in FIG. 13, when the optical axis direction distance of the measurement optical system 23 is properly set with respect to the eye 32 to be tested, the upper target image 68 and the lower target image 70 are held in alignment with respect to each other, and likewise the upper target image 69 and the lower target image 71 are held in alignment with respect to each other. On the contrary, when the distance is improperly set, the upper target images 68, 69 and the lower target images 70, 71 are split in the right and left direction as shown in FIGS. 14 and 15. This split amount corresponds to the shifted amount from the optical axis direction distance when the measurement optical system is properly set with respect to the eye 32 to be tested. By virtue of the split of the upper target images 68, 69 and the lower target images 70, 71, the so-called working distance can be accurately measured even if the split amount is small.

Figure 16:
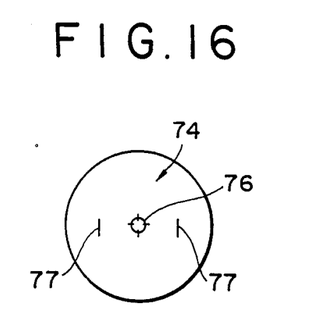
FIG. 16 is a plan view of a positioning target plate shown in FIG. 5.

The eye position detection optical system 39 includes a target image projection means 72 for projecting a target image for verifying the alignment of the measurement optical axis p with respect to the eye 32 to be tested within a plane intersecting the measurement optical axis p at right angles to the photosensitive surface 64 of the photosensitive element 50. This target image projecting means 72 generally comprises an illumination light source 73, a target plate 74 and a projection lens 75. The target plate 74 is formed at its center with a pattern 76 forming a circular cross line, and at both sides sandwiching the pattern 76 with a position target pattern 77 for showing the position of the target image when the optical axis direction distance of the measurement optical system 23 is properly set with respect to the eye 32 to be tested as shown in FIG. 16. This position target pattern 77 is formed of a fine line shaped slit. In FIGS. 13 through 15, 78 denotes a positioning target image corresponding to the pattern 76, while 79 denotes a position target image corresponding to the position target pattern 77. FIGS. 13 and 15 illustrate the properly set state of the measurement optical axis p of the measurement optical system 23 with respect to the eye 32 to be tested within a plane intersecting the measurement axis p at right angles. On the other hand, FIG. 14 illustrates the shifted state of the measurement optical axis p of the measurement optical system 23 with respect to the eye 32 to be tested within a plane intersecting the measurement optical axis p at right angles.

Figure 17:
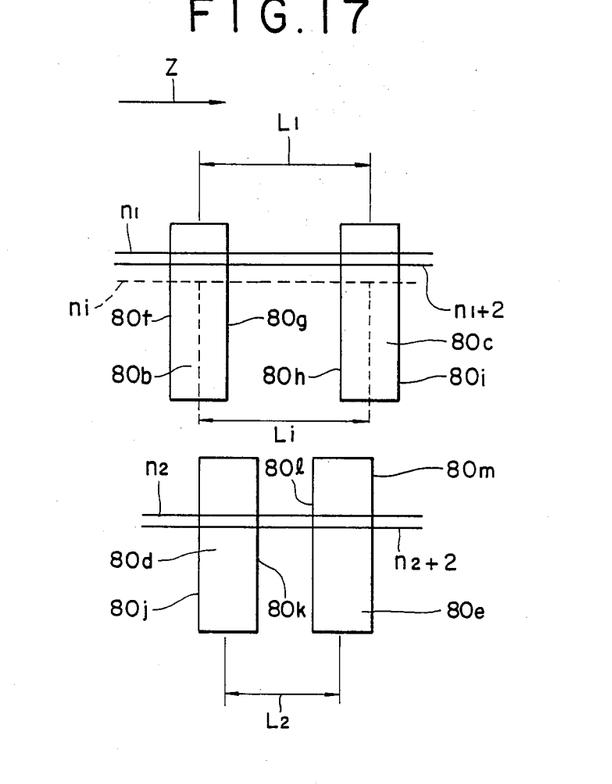
FIG. 17 is a schematic illustration for explaining how a target distance between measurement target images is obtained.

The measurement optical system 23 includes a photosensitive element 37. A photosensitive surface 38 of the photosensitive element 37 is formed with a measurement target image having a configuration corresponding to the measurement target image formed on the retina 33. The measurement target image is opto-electrically converted into an electrical signal in order to be outputted to a television monitor 79' and also to a control arithmetic portion of a measurement circuit as will be described later. FIG. 17 illustrates a measurement target image 80 formed on the photosensitive element 38 of the photosensitive surface 37. This measurement target image 80 is formed of a pair of upper slit-like rectangular images 80$b$, 80$c$ and a pair of lower rectangular images 80$d$, 80$e$. The control arithmetic portion has such a function as to obtain a distance $l_1$ between the rectangular image 80$b$ and the other rectangular image 80$c$, and the distance $l_2$ between the rectangular image 80$d$ and the other rectangular image 80$e$. This photosensitive element 37 is connected to the measurement circuit. The measurement circuit has such a function as to scan the photosensitive surface 38 to obtain the distance $l_1$ between the pair of upper target images 80$b$ and 80$c$, and the distance $l_2$ between the pair of lower target images 80$d$ and 80$e$. Symbolic reference character Z denotes the scanning direction of a scanning line.

The above-mentioned distances $l_1$ and $l_2$ are obtained by the steps as will be described hereinafter. First of all, the position of a leading edge 80$f$ of the target image 80$b$ is set as A, the position of a trailing edge 80$g$ of the target image 80$b$ as B, the position of a leading edge 80$h$ of the target image 80$c$ as C, and the position of a trailing edge 80$i$ of the target image 80$c$ as D. The positions A–D are variable here. When the distance $l_2$ between the pair of lower target images 80$d$ and 80$e$ is to be obtained, A corresponds to the position of a leading edge 80$j$ of the target image 80$d$, B likewise to the position of a trailing edge 80$k$ of the target image 80$d$, C to the position of a leading edge 80$l$ of the target image 80$e$ and D to the position of a trailing edge 80$m$ of the target image 80$e$. The distance between target images vary per every scanning line. A distance corresponding to a scanning line ni is set as li. The respective positions corresponding to this scanning line ni are represented by Ai–Di. Then, li is obtained by the following formula;

$$li = \frac{1}{2}\{(Ai + Bi) - (Ci + Di)\}$$

Figure 18:
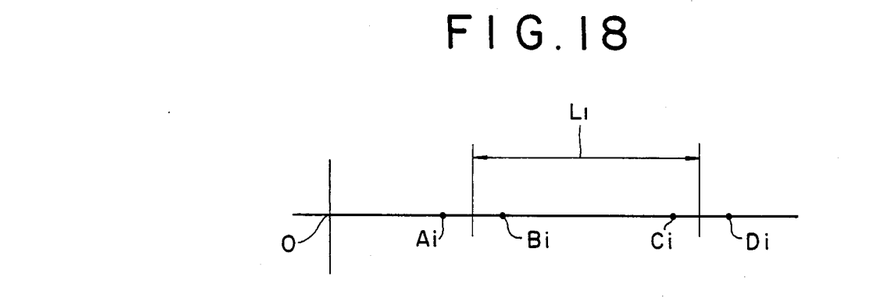
FIG. 18 is a schematic illustration for explaining how arithmetic processing in the present invention is carried out.

In order to understand the above formula, reference should be made to FIG. 18.

When this measurement is effected, li is to be obtained twice or more for a pair of target images. Scanning lines $n_1$, $n_1+2$ are used here in order to obtain the distance li between the pair of upper target images 80$b$ and 80$c$, while scanning lines $n_2$, $n_2+2$ are used in order to obtain the distance $l_2$ between the pair of lower target images 70$d$ and 70$e$. The scanning lines $n_1$, $n_1+2$, $n_2$, $n_2+2$, $\ln_1$, $l_1+2$, $\ln_2$, and $\ln+2$ are averaged by arithmetic means. That is, $$l_1 = \frac{1}{2}\{ln_1 + ln_2 + 2\} \qquad (A)$$

$$= \frac{1}{2}\left[\frac{1}{2}\{(An_1 + Bn_1) - (Cn_1 + Dn_1)\} - \frac{1}{2}\{(An_1 + 2 - Bn_1 + 2) - (Cn_1 + 2 + Dn_1 + 2)\}\right]$$

$$= \frac{1}{4}[\{(An_1 + Bn_1) - (Cn_1 + Dn_1) + \{(An_1 + 2 + Bn_1 + 2) - (Cn_1 + 2 + Dn_1 + 2)\}]$$

$$l_2 = \frac{1}{2}(ln_2 + ln_2 + 2) \qquad (B)$$

$$= \frac{1}{4}[\{(An_2 + Bn_2) - (Cn_2 + 2 + Dn_2 + 2)\}]$$

The measurement is effected by detecting the leading edge positions and the trailing edge positions of the respective target images 80$b$–80$e$, and arithmetically processing the detected positions at the control arithmetic portion. Since the steps of obtaining the distance $l_1$ between the pair of upper target images are the same as the steps of obtaining the distance $l_2$ between the pair of lower target images, only the steps with regard to obtaining the distance $l_1$ will be described hereinafter.

Figure 19:
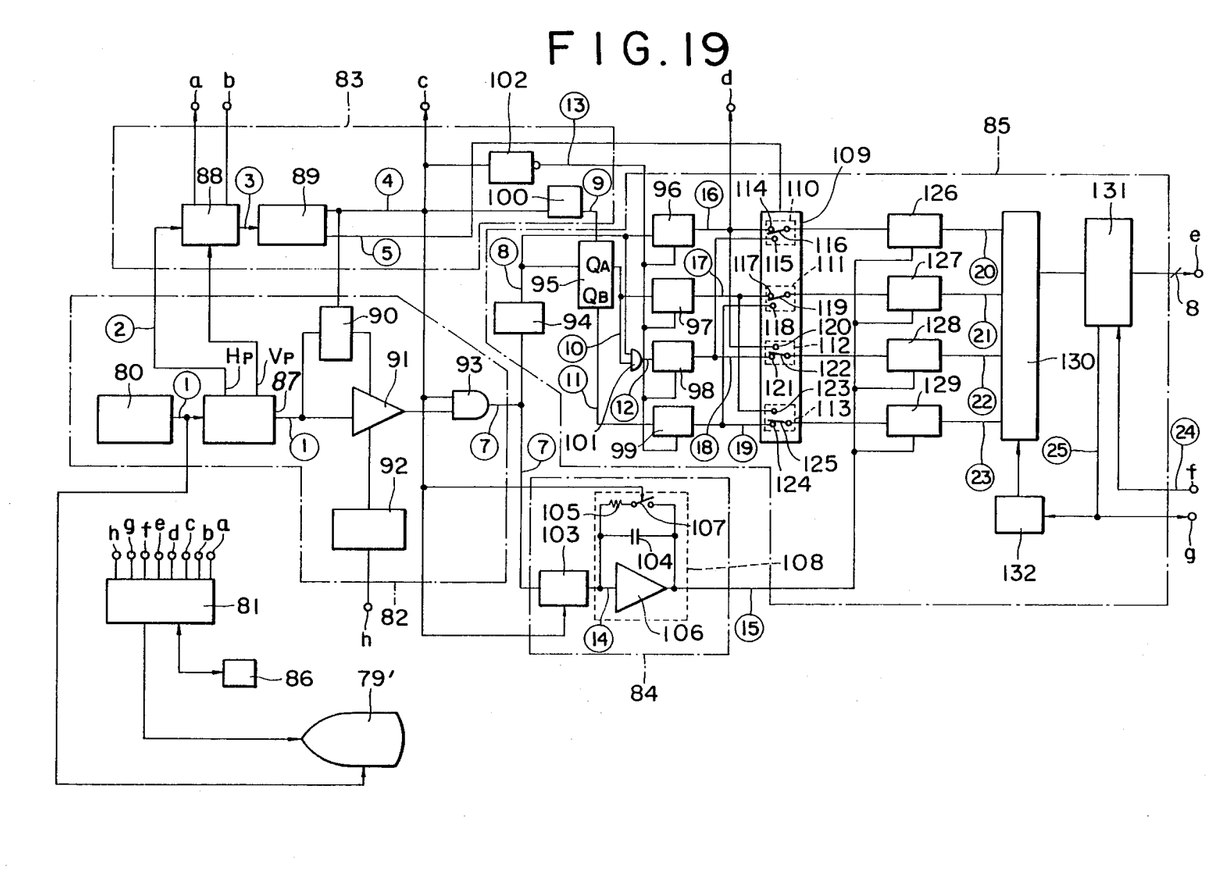
FIG. 19 is a block diagram of a measurement circuit to be used in the eye refractive power measuring apparatus of the present invention.

The measurement circuit, as shown in FIG. 19, comprises a control arithmetic portion 81, a target image signal detection circuit 82, a timing signal detection circuit 83, a reference signal formation circuit 84, a target image position detection circuit 85 and a drive circuit 86. The target image signal detection circuit 82 has a function to take off a brightness signal, corresponding to the target image transformed a an electrical signal, and convert it into a rectangular signal.

Figure 20:
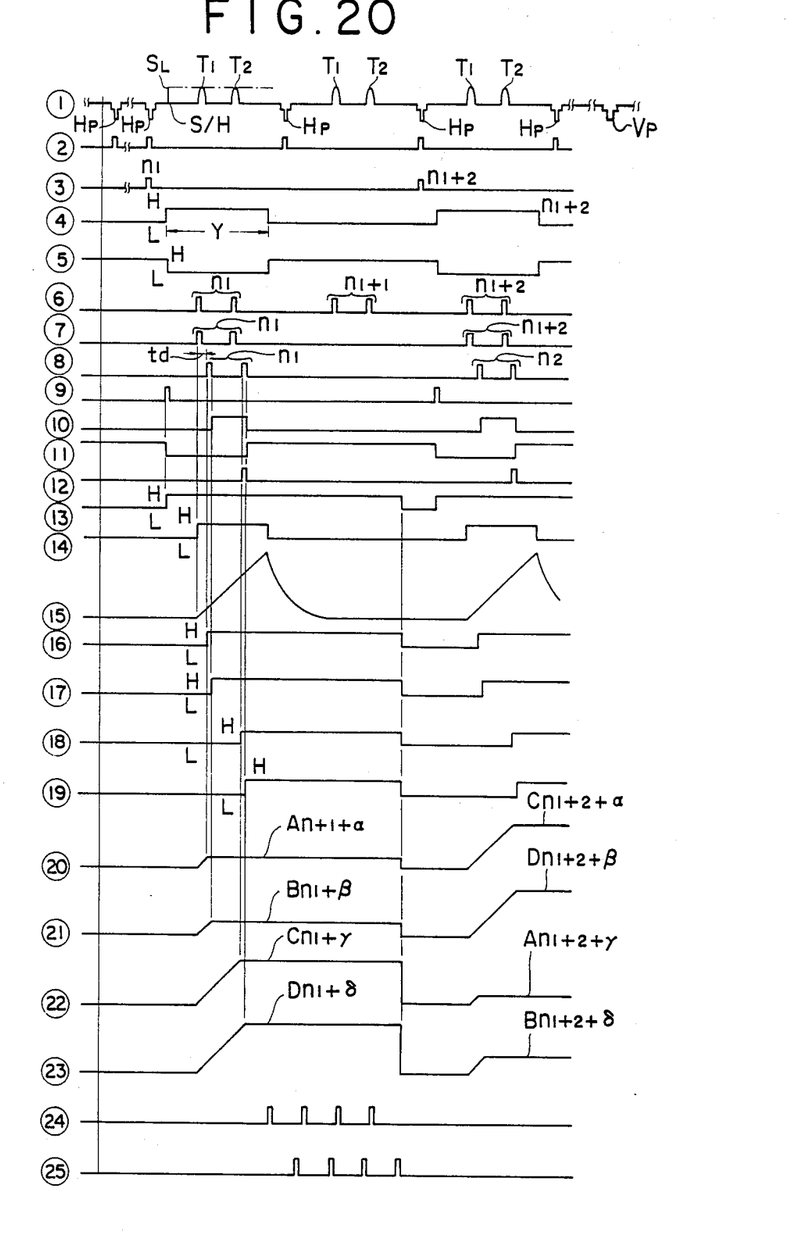
FIG. 20 is a timing chart of the measurement circuit of the eye refractive power measuring apparatus according to the present invention.
Figure 20A:
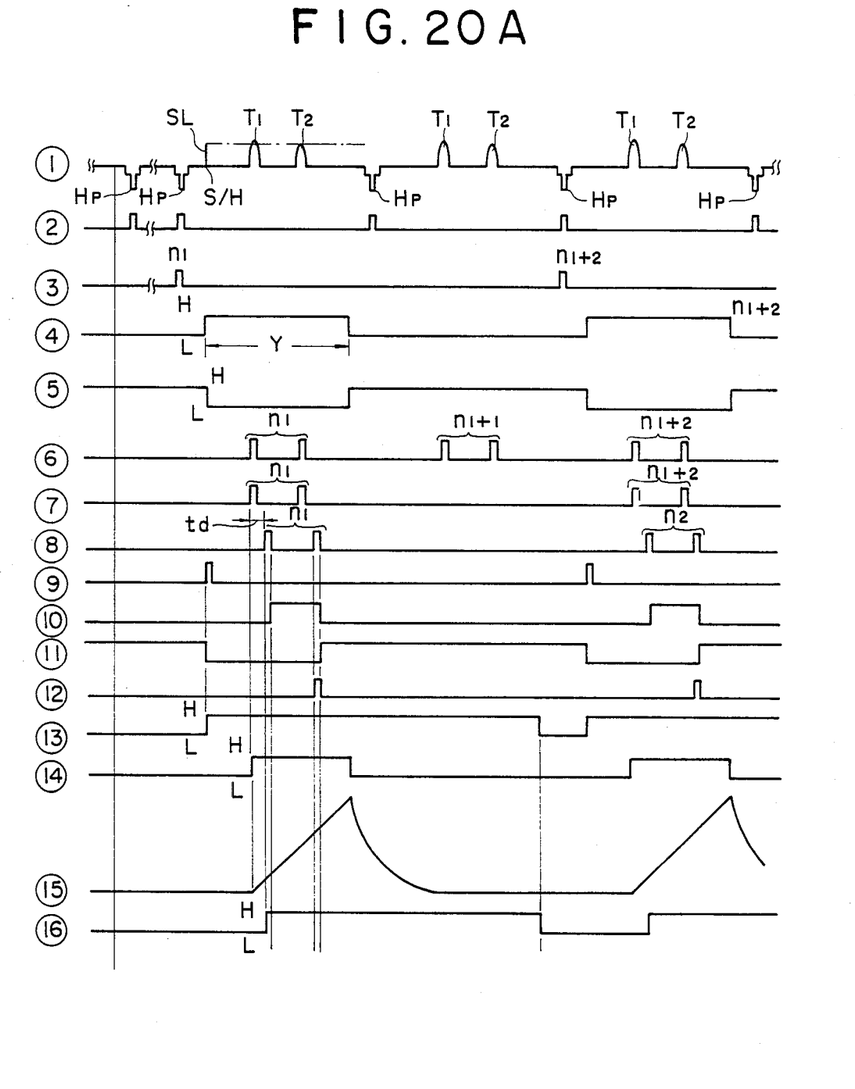
FIG. 20(A) is an enlarged upper half thereof and FIG. 20(B) is an enlarged lower half thereof.
Figure 20B:
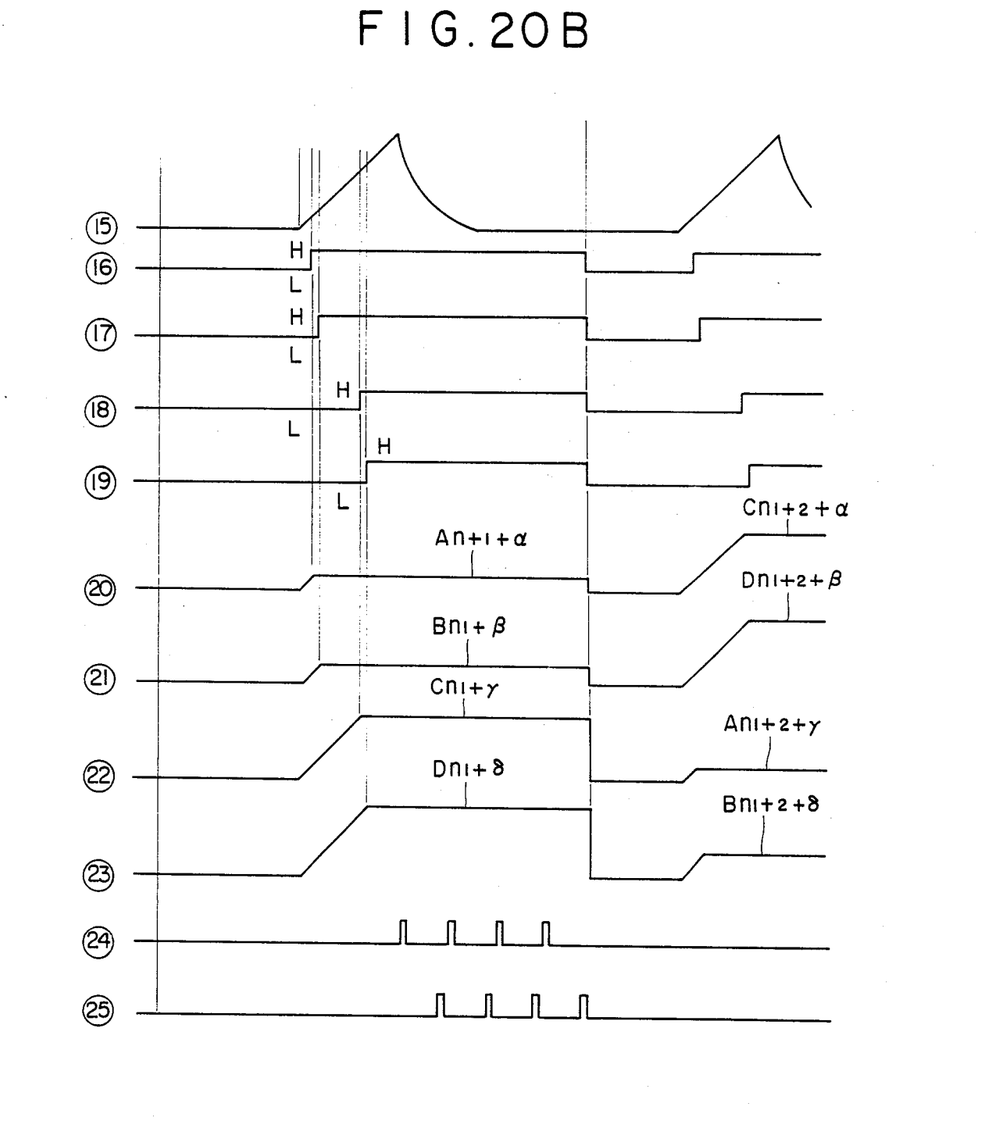

The target signal detection circuit 82 includes a synchronizing signal take-off circuit 87. The synchronizing signal take-off circuit 87 is inputted with an electrical signal outputted from the image pick-up apparatus 37. In FIG. 20, reference numeral 1 denotes this electrical signal. The electrical signal 1 includes a horizontal synchronizing signal $H_P$ and a vertical synchronizing signal $V_P$. In addition, it includes brightness signals $T_1$, $T_2$ corresponding to the target images 80$b$, 80$c$. The synchronizing signal take-off circuit 87 is adapted to take off the horizontal synchronizing signal $H_P$ and the vertical synchronizing signal $V_P$ and output the same toward a counter circuit 88. In FIG. 20, reference numeral ② denotes a horizontal synchronizing signal separated and taken off. The counter circuit 88 is a part of the timing signal formation circuit 83. The timing signal formation circuit 83 has such a function as to designate the operation timing of the target image position detection circuit 85 and the control arithmetic portion 84.

The counter circuit 88 has such a function as to designate a scanning line when a measurement is effected. This counter circuit 88 is adapted to count the number of the inputted horizontal synchronizing signals 2 to count the number of the scanning lines, and the count content is reset based on the vertical synchronizing signal $V_P$. The counter circuit 88 is connected to terminals a, b of the control arithmetic portion 81. The terminals a, b are adapted to output address signals corresponding to scanning line numbers $n_1$, $n_2$ toward the counter circuit 88. The scanning line number $n_1$ corresponds to the scanning line when the distance $l_1$ between the target images 80$b$ and 80$c$ is measured, while the scanning line number $n_2$ corresponds to the scanning line when the distance $l_2$ between the target images 80d and 80e is measured. The counter circuit 88 is adapted to output a pulse signal toward a wind circuit 89 based on the address signal when the scanning line numbers are $n_1$, $n_1+2$, $n_2$, and $n_2+2$. In FIG. 20, reference numeral ⑧ denotes a signal outputted from this counter circuit 88.

The wind circuit 89 is adapted to output rectangular waves ④, ⑤ based on the pulse signal ⑧. The rectangular wave is a reverse signal of the rectangular wave ④. The rectangular wave ④ becomes from L to H based on the pulse signal ⑧, while the rectangular wave ⑤ becomes from H to L. The period Y during which the rectangular wave ④ becomes H is set such that the brightness signal, at the time when the pair of target images are separated by a maximum amount according to the focussing state, is included. The functions of these rectangular waves ④ and ⑤ will be described later.

The electrical signal ① is inputted to a sample hold circuit 90 and a comparator 91 through the synchronizing signal take-off circuit 87. The sample hold circuit 90 has such a function as to fix the electrical signal level ① as an S/H level based on the stand-up of the rectangular wave ④. The comparator 91 is inputted with a slice level signal for deciding the slice level SL of brightness signals $T_1$, $T_2$. This slice level signal is outputted from a slice level decision circuit 92. This slice level decision circuit 92 is connected to the terminal h of the control arithmetic portion 81 and controlled by the control arithmetic portion 81. The comparator 91 has such a function as to convert the brightness signals $T_1$, $T_2$ into the rectangular wave 6 based on the sample hold circuit 90 and the slice level decision circuit 92. Reference numeral ⑥ of FIG. 20 denotes a rectangular wave corresponding to the scanning line numbers $n_1$, $n_1+2$.

The comparator 91 is connected to one terminal of an AND circuit 93. The other terminal of the AND circuit 93 is connected with the wind circuit 89. The AND circuit 93 has such a function as to remove unnecessary signals for measurement including the rectangular wave corresponding to the scanning line number n+1 from the rectangular waves ⑥, and take off a rectangular wave to be used for the measurement based on the rectangular wave ④. In FIG. 20, reference numeral ⑦ denotes a rectangular wave to be used for the measurement. The rectangular wave ⑦ is inputted in the reference signal formation circuit 84 and the target image position detection circuit 85. The target image position detection circuit 85 includes a delay circuit 94. The rectangular wave ⑦ is delayed by the delay circuit 94 by the time minute td. In FIG. 20, reference numeral ⑧ denotes a delayed rectangular wave. This delay circuit 94 has such a function as to adjust timewise the reference signal formation circuit 84 and the target image position detection circuit 85.

The target image position detection circuit 85 includes a count circuit 95 and latch circuits 96–99. This counter circuit 95 includes terminals $Q_A$, $Q_B$. This counter circuit 95 is connected to a reset circuit 100 constituting a part of the timing signal formation circuit 83. This reset circuit 100 is connected to the wind circuit 89 and outputs a reset pulse ⑨ to counter 95 based on the stand-up of the rectangular wave ④. The counter circuit 95 is a binary counter. The count content of counter circuit 95 is cleared by the reset pulse ⑨. The reset circuit 100 has such a function as to designate the count timing. The counter circuit 95 effects the counting according to the stand-up of the rectangular wave ⑧. The terminal $Q_A$ is adapted to output a rectangular wave ⑩ corresponding to the low order digit, while the terminal $Q_B$ is adapted to output a rectangular wave corresponding to the upper order digit. The stand-up of the rectangular wave ⑩ corresponds to the trailing edges 80g, 80k of the target images 80b, 80d, while the stand-up of the rectangular wave ⑪ corresponds to the retaining edges of the target images 80c, 80e.

The terminal $Q_A$ is connected to the latch circuit 97 and one terminal of the AND circuit 101. The terminal $Q_B$ is connected to the latch circuit 99. The output end of the AND circuit 101 is connected to the latch circuit 98. The latch circuit 95 and the other terminal of the AND circuit 101 are connected to the delay circuit 94. The AND circuit 101 is adapted to output rectangular waves corresponding to the target images 80c, 80e based on the rectangular wave ⑧ and rectangular wave ⑩. In FIG. 20, reference numeral ⑫ denotes a rectangular wave outputted from this AND circuit 101.

The latch circuits 96–99 have such functions as to convert the respective leading edge positions and trailing edge positions of the target images 80b–80e into time for storage. The latch circuits 96–99 are cleared of the stored content by a mono-stable circuit 102 forming a part of the timing signal formation circuit 83. The rectangular wave ④ is inputted in the mono-stable circuit 102. When the rectangular wave ④ becomes from L to H, it is risen from L to H. In FIG. 20, reference numeral ⑬ denotes a rectangular wave outputted from this mono-stable circuit 102. The latch circuits 96–99 assume a latchable state when the output of the mono-stable circuit 102 becomes from L to H. This output will be described later. Next, the reference signal formation circuit 84 will be described.

The reference signal formation circuit 84 has such a function as to generate a reference voltage for converting the leading edge position and the trailing edge position detected timewise into voltages. This reference signal formation circuit 84 comprises a latch circuit 103, a condenser 104, a resistor 105, an operational amplifier 106 and a switch 107. The latch circuit 103 is connected to the wind circuit 89 and the AND circuit 93. It becomes from L to H based on the stand-up of the first inputted rectangular wave between a pair of rectangular waves ⑦ and becomes from H to L based on the stand-up of the rectangular wave ④ from H to L. In FIG. 20, reference numeral ⑭ denotes a rectangular wave outputted from this latch circuit 103. The condenser 104, resistor 105, operational amplifier 106 and switch 107 constitute an integrating circuit 108. The integrating circuit 108 is adapted to start integration based on the stand-up of the rectangular wave ⑭ from L to H. The integrating circuit 108 is adapted to output an integrating voltage as shown by reference numeral ⑮ in FIG. 20. This integrating voltage ⑮ is linearly increased while the rectangular wave ⑭ is H. When the rectangular wave ④ becomes from H to L, the switch 102 is shut, and the integrating voltage ⑮ is decreased according to charge and discharge characteristic. The switch 107 is opened while the rectangular wave ④ is H. The linear portion of the integrating voltage is used when the measurement is effected.

The latch circuit 96 becomes from L to H by the stand-up of the first inputted pulse of the rectangular wave ⑧ and becomes from H to L by the sit-down of the rectangular wave ⑬. In FIG. 20, reference numeral ⑯ denotes a rectangular wave outputted from this latch circuit 96. The latch circuit 97 becomes from L to H by the stand-up of the pulse signal ⑩ outputted from the terminal $Q_A$ and becomes from H to L by the sit-down of the rectangular wave ⑬. In FIG. 20, reference ⑰ denotes a rectangular wave outputted from this latch circuit 97. The latch circuit 98 becomes from L to H by the stand-up of the rectangular wave ⑫ outputted from the AND circuit 101 and becomes from H to L by the sit-down of the rectangular wave ⑬. In FIG. 20, reference numeral ⑱ denotes a rectangular wave outputted from this latch circuit 98. The latch circuit 99 becomes from L to H by the stand-up of the rectangular wave ⑪ outputted from the terminal $Q_B$ and becomes from H to L by the sit-down of the rectangular wave ⑬. In FIG. 20, reference numeral ⑲ denotes a rectangular wave outputted from this latch circuit 99. The stand-up of the rectangular wave ⑯ corresponds to the leading edges of 80f, 80j of the target images 80b, 80d, while the stand-up of the rectangular wave ⑰ corresponds to the trailing edges 80g, 80k of the target images 80b, 80d. The stand-up of the rectangular wave ⑱ corresponds to the leading edges 80h, 80e of the target images 80c, 80e, while the stand-up of the rectangular wave ⑲ corresponds to the trailing edges 80i and 80m of the target images 80c, 80e.

The outputs of the respective latch circuits 96–99 are inputted in a selector circuit 109 functioning as a switch-over portion. This selector circuit 109 includes switches 110–113. The switch 110 has fixed contacts 114, 115 and a movable contact 116. The switch 111 has fixed contacts 117, 118 and a movable contact 119. The switch 112 has fixed points 120, 121 and a movable contact 122. The switch 113 has fixed contacts 123, 124, and a movable contact 125. The selector circuit 109 is inputted with the rectangular wave ⑤ outputted from the wind circuit 89. The selector circuit 109 has such a function as to switch over the movable contacts 116, 119, 122, 125 among the fixed contacts 114, 115, 117, 118, 120, 121, 123, 124 based on this rectangular wave ⑤. The movable contact 116 is connected to the contact 114 and the contact 115 in turn every time the rectangular wave ⑤ stands up. The movable contact 119 is connected to the contact 117 and the contact 118 in turn every time the rectangular wave ⑤ stands up. The movable contact 122 is connected to the contact 121 and the contact 120 in turn every time the rectangular wave ⑤ stands up. The movable contact 125 is connected to the contact 124 and the contact 125 in turn every time the rectangular wave ⑤ stands up. The wind circuit 89 has such a function as to designate the switch-over timing of the switches 110–113 also.

The fixed contact 114 is connected to the latch circuit 96. The fixed contact 115 is connected to the latch circuit 97. The fixed contact 117 is connected to the latch circuit 97. The fixed contact 118 is connected to the latch circuit 99. The fixed contact 120 is connected to the latch circuit 96. The fixed contact 121 is connected to the latch circuit 98. The fixed contact 123 is connected to the latch circuit 97. The fixed contact 124 is connected to the latch circuit 99. The movable contact 116 is connected to the sample hold circuit 116. The movable contact 119 is connected to the sample hold circuit 127. The movable contact 122 is connected to the sample hold circuit 128. The movable contact 125 is connected to the sample hold circuit 129.

The sample hold circuit 126 is adapted to hold the voltage shown by reference numeral ⑳ based on the rectangular waves ⑯, ⑱. The sample hold circuit 127 is adapted to hold the voltage shown by reference numeral ㉑ based on the rectangular waves ⑰, ⑲. The sample hold circuit 128 is adapted to hold the voltage shown by reference numeral ㉒ based on the rectangular waves ⑯, ⑱. The sample hold circuit 129 is adapted to hold the voltage shown by reference numeral ㉓ based on the rectangular waves ⑰, ⑲. The sample hold circuits 126–129 have such functions as to convert the respective leading edge and trailing edge positions into voltage values. In the voltages ⑳ – ㉓, $An_1$ denotes a voltage corresponding to the position of the leading edge 80f of the target image 80b at the scanning line number $n_1$. $Bn_1$ denotes a voltage corresponding to the position of the retailing edge 80g of the target image 80b at the scanning line number $n_1$. $Cn_1$ denotes a voltage corresponding to the position of the leading edge 80h of the target image 80c at the scanning line number $n_1$. $Dn_1$ denotes a voltage corresponding to the position of the trailing edge 80i of the target image 80c at the scanning line number $n_1$. In the scanning line number $n_1+2$, the voltages corresponding to the respective positions are each made with an extension $n_1+2$ to the symbolic reference characters A–B.

The sample hold circuit 126 here is adapted to hold a voltage $An_1$ corresponding to the position of the leading edge 80f of the target image 80b when the scanning line number is $n_1$, and hold a voltage $Cn_1+2$ corresponding to the position of the leading edge 80f of the target image 80b, when the scanning line number is $n_1+2$. The sample hold circuit 127 is adapted to hold a voltage $Bn_1$ corresponding to the position of the trailing edge 80g of the target image 80b when the scanning line number is $n_1$, and hold a voltage $Dn_1+2$ corresponding to the position of the trailing edge 80i of the target image 80c when the scanning line number is $n_1+2$. The sample hold circuit 128 is adapted to hold a voltage $Cn_1$ corresponding to the position of the leading edge 80h of the target image 80c when the scanning line number is $n_1$, and hold a voltage $An_1+2$ corresponding to the position of the leading edge 80f of the target image 80b when the scanning line number is $n_1+2$. The sample hold circuit 129 is adapted to hold a voltage $Dn_1$ corresponding to the position of the trailing edge 80i of the target image 80c when the scanning line number is $n_1$, and hold a voltage corresponding to the position of the trailing edge 80g of the target image 80b when the scanning line number is $n_1+2$.

These respective voltages $An_1$–$Dn_1$, and $An_1+2$–$Dn_1+2$ include error voltages $\alpha, \beta, \gamma$, and $\delta$ due to offset temperature characteristic of the respective sample hold circuits 126–129 and power source voltage fluctuation. The error voltage which the sample hold circuit 126 includes is represented by $\alpha$. The error voltage which the sample hold circuit 127 includes is represented by $\beta$. The error voltage which the sample hold circuit 128 includes is represented by $\gamma$. The error voltage which the sample circuit 129 includes is represented by $\delta$. The output voltages of the sample hold circuits 126–129 are inputted into a multiplexer 130. This multiplexer 130 has such a function as to connect the sample hold circuits 126–129 to an A/D converter 131 one after the other.

The A/D converter 131 has such a function as to convert the output voltages of the sample hold circuits 126-129 to digital signals one after the other and output the same to the terminal e of the control arithmetic portion 81 through an eight bit line. This converter 131 is inputted with an A/D conversion start signal ㉔ from the terminal f of the control arithmetic portion 81. This A/D conversion start signal ㉔ is outputted from the control arithmetic portion 81 based on the sit-down of the rectangular wave ④ inputted in the control arithmetic portion 81 through the terminal c. This A/D conversion start signal ㉔ is formed of a series of four pulses corresponding to the number of the sample hold circuits 126-129. The A/D converter 131 outputs an A/D conversion finish signal ㉕ every time the A/D conversion is finished. This A/D conversion finish signal ㉕ is inputted into a select circuit 132 and also into the control arithmetic portion through the terminal g. The output of this select circuit 132 is inputted into the multiplexer 130. The select circuit 132 has such a function as to connect the multiplexer 130 to the respective sample hold circuits 126-129 based on the finish signal ㉕ one after the other. The control arithmetic portion 81 starts arithmetic processing for obtaining the distances $l_1$, $l_2$ between the target images based on the final A/D conversion finish signal.

The following formula (A) is used in the arithmetic processing for obtaining the target distance $l_1$, while the following formula (B) is used in the arithmetic processing for obtaining the target distance $l_2$. The arithmetic processing for obtaining the target distance $l_2$ will be described here taking into consideration the fact that the sample hold circuits 126-129 include the respective error voltages $\alpha$–$\delta$, $$l_1 = \frac{1}{4} [\{(An_1 + \alpha + Bn_1 + \beta) - (Cn_1 + \gamma + Dn_1 + \alpha)\} +$$

$$\{(An_1 + 2 + \gamma + Bn_1 + 2 + \delta) - (Cn_1 + \alpha + Dn_1 + 2 + \beta)\}]$$

If this formula is straightened;

$$l_1 = \frac{1}{4} [\{(An_1 + Bn_2) - (Cn_1 + Dn_1)\} +$$

$$\{(An_1 + 2 + Bn_1 + 2) - (Cn_1 + 2 + Dn_1 + 2)\}]$$

That is, the error voltages $\alpha$–$\delta$ which the sample hold circuits 126-129 include are eliminated by this arithmetic processing. Based on such detected target image distances $l_1$, $l_2$, the measurement target plate 25 and the relay lens 35 are integrally moved by the drive control circuit 86 to a position where a relation of $l_1 = l_2$ is obtained, i.e., a position where the measurement target image is focussed on the retina 33 of the eye 32 to be tested. Based on this moved amount, the refractivity of the eye 32 to be tested is computed.

The measurement circuit is commonly used for detecting the target image 67 for use in adjusting the optical axis direction distance. The electrical signal optoelectrically converted by the photosensitive element 37 is inputted into the television monitor 79' and also into the target image signal detection circuit 82. The steps for treating the target image 67 for the use of adjusting the optical axis direction distance is generally the same as the steps for treating the measurement target image, with the exception that the steps for treating the measurement target image uses one of two scanning lines, while the steps for treating the target image 67 uses each one of the scanning lines $n_1$, $n_2$.

Figure 21:
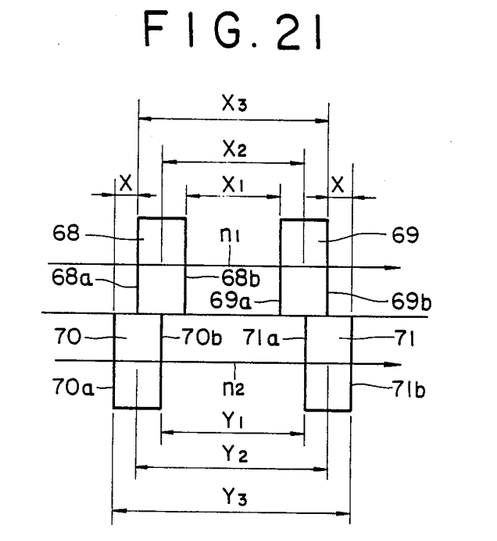
FIG. 21 is a schematic illustration for explaining how a target distance between target images for an optical axis direction distance is obtained.
Figure 22:
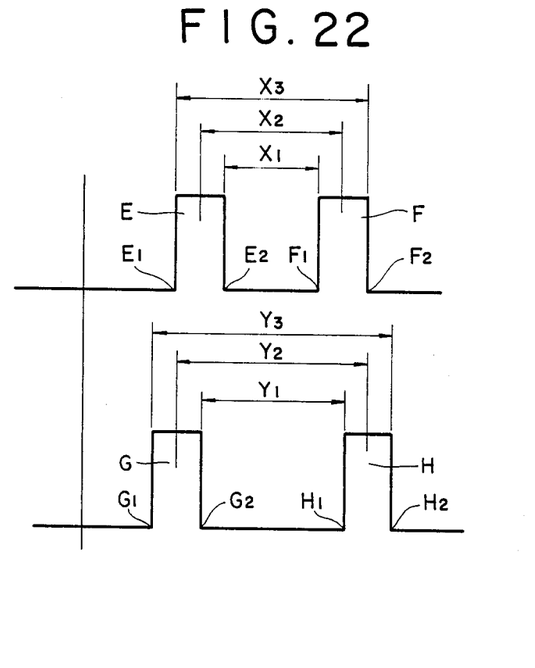
FIG. 22 is a schematic illustration of a pulse corresponding to the target images shown in FIG. 21.

As shown in FIG. 21, when an average target is $X_2$ between the upper target images 68 and 69 a pair of pulses E, F shown in FIG. 22 are obtained by one scanning line $n_1$. Likewise, when an average target distance between the lower target images 70 and 71 is detected, a pair of pulses G, F shown in FIG. 22 are obtained by one scanning line $n_2$ shown in FIG. 22. These pairs of pulses E, F, G, H correspond to the initial pulse as shown by reference numeral ⑦ in FIG. 20. The standing positions $E_1$, $F_1$, $G_1$, $H_1$ of these pulses E, F, G, H correspond to the leading edges 68a, 69a of the upper target images 68, 69, and the leading edges 70a, 71a of the lower target images 70, 71, respectively.

On the other hand, the sitting positions $E_2$, $F_2$, $G_2$, $H_2$ correspond to the trailing edges 68b, 69b of the upper target images 68, 69 and the trailing edges 70b, 71b of the lower target images 70, 71, respectively. The foregoing is also the same as the steps for treating the measurement target image. The standing positions $E_1$, $F_1$, $G_1$, $H_1$ and the sitting positions $E_2$, $F_2$, $G_2$, $H_2$ of the pulses E, F, G, H, which are the same as the steps for treating the measurement target image, are converted into pulses after being converted into voltages by the measurement circuit. The average target distances $X_2$, $Y_2$ are obtained by inputting the pulsed signal into the arithmetic control portion 81.

The average target distance $X_2$ is computed by arithmetically averaging the distance $X_3$ from the stand-up position $E_1$ of the pulse E to the sit-down position $F_2$ of the pulse F, and the distance $X_1$ from the sit-down position $E_2$ of the pulse E to the stand-up position $F_1$ of the pulse F. The average target distance $Y_2$ is computed by arithmetically averaging the distance $Y_3$ from the stand-up position $G_1$ of the pulse G to the sit-down position $H_2$ of the pulse H, and the distance $Y_1$ from the sitting position $G_2$ of the pulse G to the standing position $H_1$ of the pulse H. Based on these average target distances $X_2$ and $Y_2$, the shifted amount 2X is obtained. This shifted amount 2X corresponds to the shifted amount from the proper optical axis distance. By the way, the optical axis distance error in (mm), the measured refractivity D (diopter) and the refractivity $D_D$ (diopter) after correcting the optical axis distance error are held in the following relation.

$$D_D = \frac{1000 \times D}{1000 + \Delta \times D}$$

Based on this relation, the arithmetic control portion 81 computes $D_D$ from the measured $\Delta$ and D. It also functions as correction means for correcting the measurement error of the refractivity.

As described in the foregoing, by paying attention to the fact that there exists a correlation between a shifted amount from the optical axis direction distance when the measurement optical system is properly set with respect to the eye to be tested, and a measurement error produced in the measurement result of the eye to be tested, the shifted amount from the optical axis direction distance when the measurement optical system is properly set with respect to the eye to be tested is detected. Based on such detected result, correction means for correcting the measurement result of the eye to be tested is provided. Accordingly, even if the optical axis direction distance of the measurement optical system is not strictly adjusted with respect to the eye to be tested, occurrence of a measurement error due to improper setting of the measurement optical system with respect to the eye to be tested can be substantially prevented, thereby providing a speedy and accurate measurement of the eye to be tested.

While a particular embodiment of the present invention has been shown in the drawings and described above, it will be apparent that many modifications may be made in the form, arrangement and positioning of the various constituent elements of the apparatus. In consideration thereof, it should be understood that the preferred embodiment of this invention disclosed herein is intended to be illustrative and not intended to limit the scope of the present invention as defined by the appended claims.

We claim:

1. In an eye refractive power measuring apparatus including a measurement system for projecting a measurement target image to the retina of an eye to be tested and measuring the refractivity of the eye to be tested by detecting the focussing state of the measurement target image, the improvement comprising:
   an eye position detection means for detecting a shifted amount from a reference position of the eye to be tested in the axial direction of the measuring system; and
   correction means for correcting a measurement result of said refractivity based on said detected shifted amount.

2. An eye refractive power measuring apparatus according to claim 1, wherein said eye position detection means includes target image projection means for projecting a flux of target rays toward the eye to be tested, and a target image formation system for forming a reflection target image by using said flux of target rays reflected from the cornea of the eye to be tested.

3. An eye refractive power measuring apparatus according to claim 2, wherein said reflection target image is formed on an image pick-up apparatus, and said reflection target image formation position is detected according to an electrical signal from said image pick-up apparatus to detect a shifted amount from the reference position of the eye to be tested.

4. An eye refractive power measuring apparatus according to claim 2, wherein said target image projection means is adapted to project the target image by splitting said flux of target rays into two portions according to two kinds of polarization ingredients of light having different polarization direction with respect to each other, and said target image formation means is adapted to have said target flux of rays reflected by said cornea of the eye to be tested form an image on an imaging surface through two different optical paths, one of said different optical paths being provided with an analyzer adapted to transmit light having only one of said two kinds of polarization ingredients, the other optical path being provided with an analyzer adapted to transmit light having only the other kind of polarization ingredient.

* * * * *